United States Patent
Okuda

(10) Patent No.: US 9,402,599 B2
(45) Date of Patent: Aug. 2, 2016

(54) ULTRASOUND PROBE AND ULTRASOUND DIAGNOSTIC IMAGING APPARATUS

(71) Applicant: KONICA MINOLTA, INC., Chiyoda-ku, Tokyo (JP)

(72) Inventor: Shuhei Okuda, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 80 days.

(21) Appl. No.: 14/321,266

(22) Filed: Jul. 1, 2014

(65) Prior Publication Data

US 2015/0011881 A1 Jan. 8, 2015

(30) Foreign Application Priority Data

Jul. 4, 2013 (JP) .................................. 2013-140372

(51) Int. Cl.
*A61B 8/08* (2006.01)
*A61B 8/00* (2006.01)
*G10K 11/00* (2006.01)
*B06B 1/06* (2006.01)

(52) U.S. Cl.
CPC ............. *A61B 8/4444* (2013.01); *A61B 8/4483* (2013.01); *B06B 1/067* (2013.01); *G10K 11/002* (2013.01)

(58) Field of Classification Search
CPC .. A61B 8/4444; A61B 8/4483; A61B 8/4405; B06B 1/0622; B06B 1/067
See application file for complete search history.

(56) References Cited

U.S. PATENT DOCUMENTS

| | | | | |
|---|---|---|---|---|
| 5,212,671 A * | 5/1993 | Fujii | ..................... | B06B 1/0685 310/335 |
| 6,685,647 B2 | 2/2004 | Savord et al. | | |
| 2007/0108872 A1* | 5/2007 | Shibamoto | ............ | B06B 1/0622 310/322 |
| 2009/0069689 A1* | 3/2009 | Isono | .................... | B06B 1/0629 600/459 |
| 2012/0163131 A1* | 6/2012 | Kennedy | ............... | B06B 1/0611 367/157 |
| 2012/0313486 A1* | 12/2012 | Jung | ...................... | G10K 11/02 310/335 |
| 2013/0085396 A1* | 4/2013 | Isono | ................... | A61B 8/4455 600/472 |
| 2013/0090561 A1* | 4/2013 | Kusukame | ............... | A61B 8/14 600/443 |

FOREIGN PATENT DOCUMENTS

JP 60185499 A 9/1985

\* cited by examiner

*Primary Examiner* — Baisakhi Roy
(74) *Attorney, Agent, or Firm* — Holtz, Holtz & Volek PC

(57) ABSTRACT

Disclosed is an ultrasound probe including a piezoelectric device which transmits and receives ultrasound, n layers of acoustic matching layers provided on a front side of the piezoelectric device, n layers meaning two layers or more, an acoustic lens which is provided on a front side of the acoustic matching layers and an acoustic reflecting layer which is provided on a back side of the piezoelectric device.

4 Claims, 4 Drawing Sheets

ULTRASOUND PROBE AND ULTRASOUND DIAGNOSTIC IMAGING APPARATUS

BACKGROUND OF THE INVENTION

1. Field of the Invention

The present invention relates to an ultrasound probe and an ultrasound diagnostic imaging apparatus.

2. Description of Related Art

Since ultrasound allows to examine inside of a subject in a non-destructive and harmless way, it has been applied in various fields such as inner defect examination, disease diagnosis and the like. As one example, ultrasound is applied to an ultrasound diagnostic imaging apparatus which visualizes the inner condition of a subject on the basis of a received signal generated from reflection ultrasound from inside of the subject by scanning inside the subject with ultrasound.

Such ultrasound diagnostic imaging apparatus is provided with an ultrasound probe which transmits and receives ultrasound to and from a subject. The ultrasound probe is provided with a plurality of piezoelectric devices each of which generates ultrasound by vibrating mechanically based on a driving signal and generates a received signal by receiving reflection ultrasound caused by the acoustic impedance difference in the subject by utilizing the piezoelectric phenomena.

The ultrasound probe is provided with an acoustic lens which focuses the ultrasound output from the piezoelectric devices in a slice direction and an acoustic matching layer which is arranged between the piezoelectric devices and the acoustic lens and which matches the acoustic impedance of the piezoelectric devices and the subject. Further, the ultrasound probe is provided with a backing layer for reflecting, attenuating and absorbing the ultrasound which is emitted backward from the ultrasound probe, the backing layer being provided on the back side of the piezoelectric devices. Here, it is known that by providing three or more acoustic matching layers, sensitivity and responsiveness of the ultrasound probe can be improved (for example, see JP Shou60-185499).

With respect to such ultrasound probe, there is known a technique which increases the ultrasound energy to be output frontward by providing an acoustic reflecting layer between the piezoelectric devices and the backing layer and reflecting the ultrasound output from the back of the piezoelectric devices toward front (for example, see U.S. Pat. No. 6,685,647). In order to improve its sensitivity and resolution in terms of distance direction, it is expected that the ultrasound probe has characteristics such as broadband, low loss and low ripple.

However, if an acoustic reflecting layer is further provided in the ultrasound probe whose overall layer thickness has increased by being provided with a plurality of acoustic matching layers, there may be a case where ripples are generated due to ultrasound reflecting in the ultrasound probe and unwanted resonance being included in the transmission and reception band of the ultrasound output from the ultrasound probe. In such case, there is a problem that the quality of the ultrasound image to be generated drops.

SUMMARY OF THE INVENTION

An object of the present invention is to provide an ultrasound probe by which an ultrasound image of high quality can be obtained and an ultrasound diagnostic imaging apparatus provided with the ultrasound probe.

In order to realize at least one of the above objects, an ultrasound probe reflecting one aspect of the present invention includes a piezoelectric device which transmits and receives ultrasound, n layers of acoustic matching layers provided on a front side of the piezoelectric device, n layers meaning two layers or more, an acoustic lens which is provided on a front side of the acoustic matching layers and an acoustic reflecting layer which is provided on a back side of the piezoelectric device, and when $t_d$ refers to a layer thickness of the acoustic reflecting layer, $t_p$ refers to a layer thickness of the piezoelectric device, $t_{m(1)}, t_{m(2)} \ldots t_{m(n)}$ respectively refer to thicknesses of the acoustic matching layers, a $1^{st}$ layer to a $n^{th}$ layer, counting from the piezoelectric device, $\lambda_{cd}$ refers to a wavelength of ultrasound at a center frequency $f_c$ of a transmission and reception band of the ultrasound probe that transmits inside the acoustic reflecting layer, $\lambda_{cp}$ refers to a wavelength of the ultrasound at the frequency $f_c$ that transmits inside the piezoelectric device and $\lambda_{cm(1)}, \lambda_{cm(2)} \ldots \lambda_{cm(n)}$ respectively refer to wavelengths of the ultrasound at the frequency $f_c$ that transmits inside the acoustic matching layers, the $1^{st}$ layer to the $n^{th}$ layer, counting from the piezoelectric device, the following formula (1) is fulfilled $$\left( \frac{t_d}{\lambda_{cd}} + \frac{t_p}{\lambda_{cp}} + \frac{t_{m(1)}}{\lambda_{cm(1)}} + \frac{t_{m(2)}}{\lambda_{cm(2)}} + \ldots + \frac{t_{m(n)}}{\lambda_{cm(n)}} \right) \leq \frac{3}{4}. \quad (1)$$

Preferably, the ultrasound probe comprises three or more acoustic matching layers.

According to another aspect of the present invention, an ultrasound diagnostic imaging apparatus includes the ultrasound probe described above, which outputs transmission ultrasound toward a subject in accordance with a drive signal and which outputs a received signal by receiving reflection ultrasound from the subject, and an image generating unit which generates ultrasound image data for displaying an ultrasound image on a basis of the received signal output from the ultrasound probe.

BRIEF DESCRIPTION OF THE DRAWINGS

The present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

Figure 1:
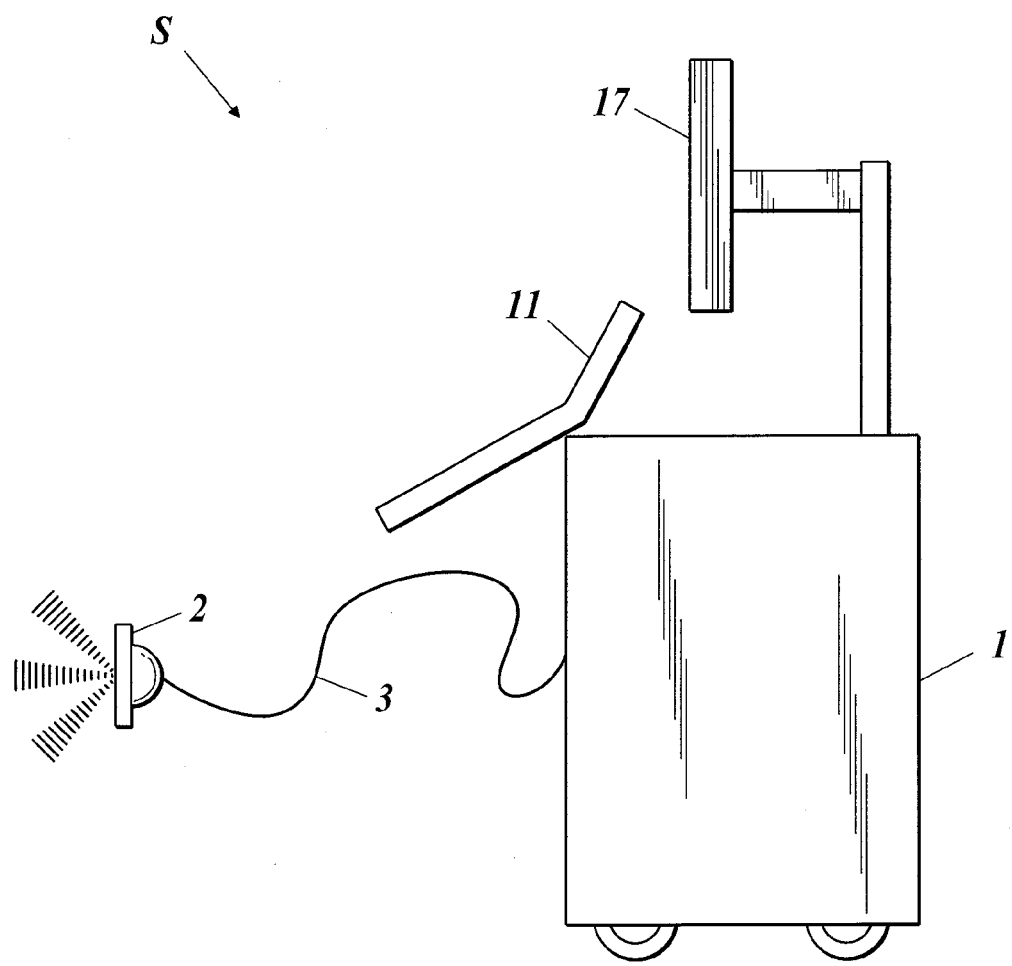
FIG. 1 shows an outer structure of an ultrasound diagnostic imaging apparatus.

Hereinafter, an ultrasound diagnostic imaging apparatus according to an embodiment of the present invention will be described with reference to the drawings. However, the scope of the present invention is not limited to the examples shown in the drawings. In the following description, same reference numerals are used for the parts having the same functions and configurations, and their descriptions are omitted.

Figure 2:
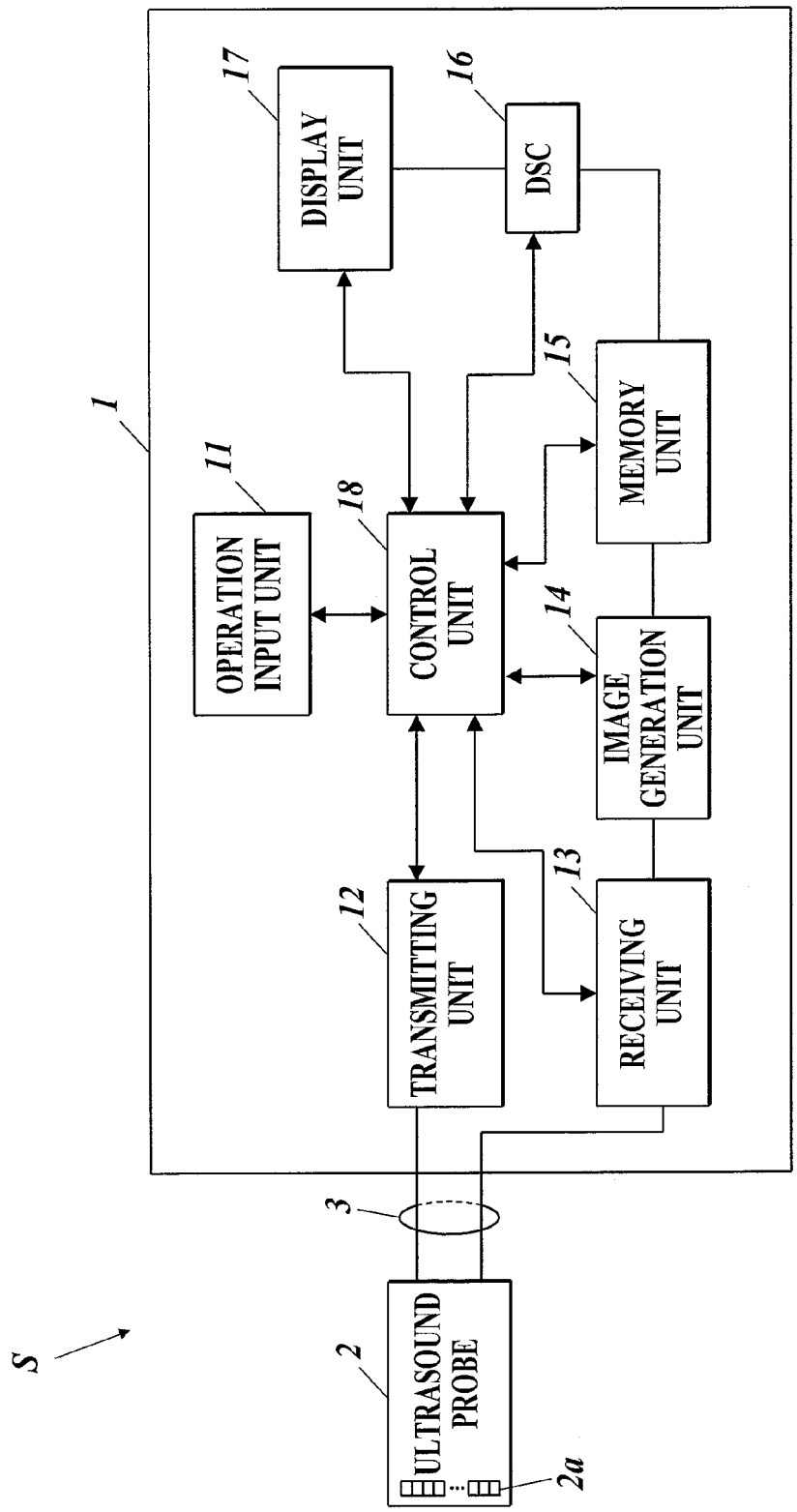
FIG. 2 is a block diagram showing an outline structure of the ultrasound diagnostic imaging apparatus.

As shown in FIGS. 1 and 2, the ultrasound diagnostic imaging apparatus S according to the embodiment includes an ultrasound diagnostic imaging apparatus main body 1 and an ultrasound probe 2. The ultrasound probe 2 transmits ultrasound (transmission ultrasound) to a subject such as a living body (not shown in the drawings) and receives reflection wave (reflection ultrasound: echo) which is the ultrasound reflected off the subject. The ultrasound diagnostic imaging apparatus main body 1 is connected with the ultrasound probe 2 via a cable 3. The ultrasound diagnostic imaging apparatus main body 1 transmits a drive signal which is an electric signal to the ultrasound probe 2 to make the ultrasound probe 2 transmit transmission ultrasound to a subject and further, visualizes, as an ultrasound image, the inside condition of the subject on the basis of a received signal which is an electric signal generated by the ultrasound probe 2 according to reflection ultrasound from inside the subject which is received by the ultrasound probe 2.

The ultrasound probe 2 is provided with transducers 2a formed of a piezoelectric device (after-mentioned, piezoelectric device 24). A plurality of transducers 2A are arranged in a one dimensional array in an orientation direction, for example. In the embodiment, for example, an ultrasound probe 2 having 192 transducers 2a is used. Here, the transducers 2a may be arranged in a two dimensional array. The number of transducers 2a can be set arbitrarily. In the embodiment, a linear scanning type electronic scanning probe is used as the ultrasound probe 2. However, either of an electronic scanning type or a mechanical scanning type can be used and further, either of a linear scanning type, a sector scanning type and a convex scanning type can also be used. The bandwidth of the ultrasound probe 2 can be set arbitrarily.

As shown in FIG. 2, the ultrasound diagnostic imaging apparatus main body 1 includes an operation input unit 11, a transmitting unit 12, a receiving unit 13, an image generation unit 14, a memory unit 15, a DSC (Digital Scan Converter) 16, a display unit 17 and a control unit 18, for example.

The operation input unit 11 includes various types of switches, buttons, a track-ball, a mouse, a key board and the like for inputting a command for instructing start of diagnosis and data such as personal information of a subject, and the operation input unit 11 outputs operation signals to the control unit 18.

The transmitting unit 12 is a circuit to make the ultrasound probe 2 generate transmission ultrasound by supplying driving signals which are electronic signals to the ultrasound probe 2 via the cable 3 in compliance with the control of the control unit 18. For example, the transmitting unit 12 includes a clock generation circuit, a delay circuit and a pulse generating circuit. The clock generation circuit is a circuit for generating a clock signal which determines the transmission timing and a transmission frequency of a driving signal. The delay circuit is a circuit for setting a delay time for each of the individual paths corresponding to the transducers, and for focusing the transmission beams (transmission beam forming) formed of transmission ultrasound by delaying the transmission of the driving signals for the set delay time. The pulse generating circuit is a circuit for generating pulse signals as driving signals at a predetermined cycle. The transmitting unit 12 which is configured as described above, for example, generates transmission ultrasound by driving a part of (for example, 64) the plurality of transducers 2a (for example, 192) which are continuous and aligned in the ultrasound probe 2. Then, the transmitting unit 12 performs scanning by shifting the transducers 2a, which are to be driven, in the orientation direction every time transmission ultrasound is to be generated. Further, in the embodiment, the transmitting unit 12 can make the ultrasound probe 2 generate transmission ultrasound of pulse waves in order to display an ultrasound image by the pulse Doppler system.

The receiving unit 13 is a circuit for receiving a received signal which is an electric signal from the ultrasound probe 2 via the cable 3 in compliance with the control of the control unit 18. The receiving unit 13 is provided with an amplifier, an A/D conversion circuit and a phasing addition circuit, for example. The amplifier is a circuit for amplifying the received signals at a preset amplification factor for each of the individual paths corresponding to the transducers 2a. The A/D conversion circuit is a circuit for performing analog/digital conversion (A/D conversion) of the amplified received signals. The phasing addition circuit is a circuit for adjusting time phases of the received signals to which A/D conversion is performed by applying the delay time to each of the individual paths corresponding to the transducers 2a and generating sound ray data by adding the adjusted received signals (phase addition).

The image generation unit 14 can generate B-mode image data by performing envelope detection, logarithmic amplification and the like on the sound ray data from the receiving unit 13 and performing brightness conversion by adjusting the gain, for example. In other words, B-mode image data is data where intensity of receives signals is expressed in brightness. The B-mode image data generated in the image generation unit 14 is transmitted to the memory unit 15.

The memory unit 15 is, for example, formed of a semiconductor memory such as a DRAM (Dynamic Random Access Memory). The B-mode image data transmitted from the image generation unit 14 is stored in the memory unit 15 in frame units. That is, the memory unit 15 stores ultrasound diagnostic imaging data consisting of frame units. The ultrasound diagnostic imaging data stored in the memory unit 15 is read out in compliance with the control of the control unit 18 and is transmitted to the DSC 16.

The DSC 16 converts the ultrasound diagnostic image data received from the memory unit 15 into an image signal of television signal scan mode and outputs the image signal to the display unit 17.

As for the display unit 17, display apparatuses such as a LCD (Liquid Crystal Display), a CRT (Cathode-Ray Tube) display, an organic EL (Electronic Luminescence) display, an inorganic EL display or a plasma display can be applied. The display unit 17 displays an ultrasound diagnostic image on the display screen according to the image signal output from the DSC 16. Here, a printing apparatus such as a printer can be applied instead of a display apparatus.

The control unit 18 includes a CPU (Central Processing Unit), a ROM (Read Only Memory) and a RAM (Random Access Memory), for example. The control unit 18 reads out and opens various types of programs such as a system program stored in the ROM in the RAM and collectively controls the operations of the components in the ultrasound diagnostic imaging apparatus S in compliance with the opened programs.

The ROM is formed of a semiconductor non-volatile memory, for example, and stores a system program corresponding to the ultrasound diagnostic imaging apparatus 100, various types of processing programs which can be executed on the system program and various types of data. These programs are stored in the forms of program codes which can be read by a computer and the CPU sequentially executes the operations according to the program codes.

The RAM forms a work area in which various types of programs to be executed by the CPU and data relating to these programs are to be stored temporarily.

Next, the ultrasound probe 2 according to the embodiment will be described with reference to FIG. 3.

Figure 3:
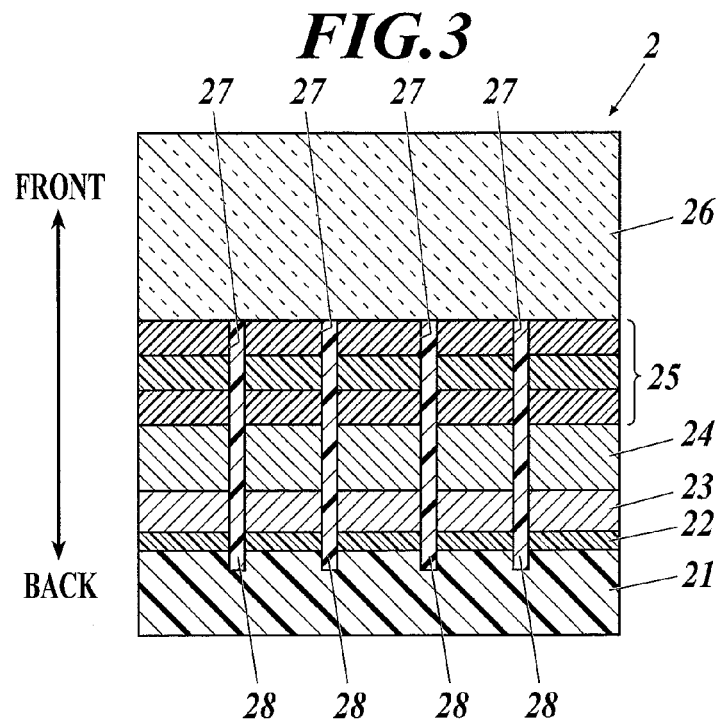
FIG. 3 is a sectional view showing an outline structure of an ultrasound probe.

As shown in FIG. 3, the ultrasound probe 2 is configured by including a backing layer 21, an acoustic reflecting layer 23 which is layered on the front side of the backing layer 21 via a flexible printed wiring board (FPC; Flexible printed circuits) 22, a piezoelectric device 24 which is layered on the front side of the acoustic reflecting layer 23, an acoustic matching layer 25 which is layered on the front side of the piezoelectric device 24 and an acoustic lens 26 which is layered on the front side of the acoustic matching layer 25, for example. A plurality of cut-out channels 27 are formed in the layered product formed of the backing layer 21, the FPC 22, the acoustic reflecting layer 23, the piezoelectric device 24 and the acoustic matching layer 25, and the cut-out channels 27 are filled with a filling material 28.

The backing layer 21 is an ultrasound absorber which supports the acoustic reflecting layer 23, the piezoelectric device 24 and the acoustic matching layer 25 and which absorbs unnecessary ultrasound. That is, the backing layer 21 is provided to be on the back side of the piezoelectric device 24, opposite to the front side thereof that transmits and receives ultrasound to and from a subject, and the backing layer 21 absorbs the ultrasound which is generated toward the opposite direction of the direction toward the subject.

As for the backing material forming the backing layer 21, natural rubber, ferrite rubber, epoxy resin, rubber composites and epoxy composites formed by adding powder of tungsten oxide, titanium oxide, ferrite or the like to the above materials, and thermoplastic resins such as vinyl chloride, polyvinyl butyral (PVB), ABS resin, polyurethane (PUR), polyvinyl alcohol (PVAL), polyethylene (PE), polypropylene (PP), polyacetal (POM), polyethylene terephthalate (PETP), fluororesin (PTFE) polyethylene glycol and polyethylene terephthalate-polyethylene glycol copolymer can be applied.

A backing material formed of a rubber composite and/or an epoxy composite is preferred, and the shape thereof can be selected arbitrarily according to the shape of the piezoelectric device 24 or the probe head including the piezoelectric device 24.

The acoustic reflecting layer 23 is a layer which reflects the ultrasound generated at the piezoelectric device 24, and the acoustic reflecting layer 23 is provided by being adhered between the piezoelectric device 24 and the FPC 22. The acoustic reflecting layer 23 reflects the ultrasound emitted toward the back to the front (toward the subject) and increases the power of the ultrasound entering the subject. The acoustic reflecting layer is for reflecting ultrasound, and it is preferred that a material having greater acoustic impedance comparing to that of the piezoelectric device 24 is used. For example, tungsten is used. Further, the acoustic reflecting layer 23 is also a material having high conductivity which electrically connects the FPC 22 and the piezoelectric device 24.

The piezoelectric device 24 includes an electrode and a piezoelectric material, and the piezoelectric device 24 can convert an electric signal into mechanical vibration and mechanical vibration into an electric signal. The piezoelectric device 24 can transmit and receive ultrasound.

Any piezoelectric material can be applied as long as the material includes a piezoelectric substance that can convert an electric signal into mechanical vibration and mechanical vibration into an electrical signal. As for the piezoelectric material, ceramics of lead zirconate titanate (PZT) system, piezoelectric ceramics of relaxor system, lead niobate system and lead titanate system, single crystals of lead zinc niobate titanate (PZNT), lead magnesium niobate titanate (PMNT) and the like are preferably used.

Further, as for the piezoelectric material, a composite piezoelectric material which is obtained by processing the above materials and adding a filler may also be used. As for the filler, organic synthetic polymer materials such as epoxy resin, silicon resin, urethane resin, polyethylene resin and polyurethane resin can be used.

On each side of the piezoelectric material, the front side and the back side, a pair of electrodes (not shown in the drawing) is provided. In each pair of electrodes, one electrode applies power voltage from the FPC 22 to the piezoelectric device 24 and the other electrode is earth connected through an FPC which is pulled out from the ground (not shown in the drawing).

As for the material to be used for the electrodes attached to the piezoelectric material, gold, (Au), platinum (Pt), silver (Ag), palladium (Pd) copper (Cu), aluminum (Al), nickel (Ni) and tin (Sn) are suggested.

As for a method to attach the electrodes to the piezoelectric material, for example, a method where a base metal of titanium (Ti) or chrome (Cr), for example, is formed to the thickness of 0.02 to 1.0 μm by spattering, and thereafter, a metal material formed of a metal whose main body is the above metallic elements and an alloy thereof and, if necessary, a partial insulating material are formed to the thickness of 0.02 to 10 μm by spattering or other appropriate method is suggested.

Other than spattering, the electrodes can be formed by forming a conductive paste which is a mixture of fine metal powder and low melting point glass by screen printing, dipping or thermal spraying. On the piezoelectric material, the electrodes are provided at the entire surface of the piezoelectric substance surface or at a part of the piezoelectric substance surface according to the shape of the ultrasound probe 2.

As described above, the electrodes of the piezoelectric device 24 are in contact with the FPC 22 and the FPC 22 and the cable 3 are electrically connected. Therefore, the drive signal which is output from the ultrasound diagnostic imaging apparatus main body 1 is input to the piezoelectric device 24 via the FPC and the received signal which is generated by the piezoelectric device 24 is output to the ultrasound diagnostic imaging apparatus main body 1.

The acoustic matching layer 25 matches the acoustic impedance between the piezoelectric device 24 and the subject and controls reflection at the interface. The acoustic matching layer 25 is adhered on the side of the piezoelectric device 24 facing toward the subject which is in the transmission and receiving direction of the ultrasound.

Each acoustic matching layer 25 has the acoustic impedance which is about the middle level between the acoustic impedance of the piezoelectric device 24 and the acoustic impedance of the subject. Two or more acoustic matching layers 25 are provided, and more preferably, three or more acoustic matching layers 25 are provided. These acoustic matching layers 25 are provided so that their acoustic impedance gradually decreases from the back side to the front side.

As for the material used for the acoustic matching layer 25, aluminum, aluminum alloy (for example, AL-Mg alloy), magnesium alloy, macole glass, glass, fused quartz, copper graphite, PE (polyethylene), PP (polypropylene), PC (polycarbonate), ABC resin, ABS resin, AAS resin, AES resin, nylon (PA6, PA6-6), PPO (polyphenylene oxide), PPS (polyphenylene sulfide: may include the ones having glass fibers), PPE (polyphenylene ether), PEEK (polyetheretherketone), PAI (polyamideimide), PETP (polyethylene terephthalate), epoxy resin, urethane resin, etc. are suggested. Preferably, a material made by evenly mixing a filler such as zinc oxide, titanium oxide, silica alumina, red iron oxide, ferrite, tungsten oxide, ytterbium oxide, barium sulfate, tungsten, molybdenum, etc. to a thermosetting resin such as epoxy resin and casting the mixture is applied. Further, the acoustic matching layers 25 may be the ones including silicon resin particles.

The layered product of the backing layer 21, the FPC 22, the acoustic reflecting layer 23, the piezoelectric device 24 and the acoustic matching layers 25 is diced by a dicing blade and a plurality of cut-out channels 27 are formed at a predetermined pitch. In such way, a plurality of transducers 2a are formed.

Further, the cut-out channels 27 are filled with a filler 28. Thereby, the front surface of the above mentioned layered product is flat.

As the material used as the filler 28, a general-purpose resin such as an epoxy resin, a silicon resin, etc. are suggested. Other additives such as a filler for physical property adjustment can be added to the above material.

The acoustic lens 26 is arranged to focus ultrasound beams by utilizing refraction and to improving resolution. That is, the acoustic lens 26 is provided on the side of the ultrasound probe 2 that contacts a subject and the acoustic lens 26 makes the ultrasound generated in the piezoelectric device 24 enter the subject in an efficient fashion. The acoustic lens 26 is the part that comes in contact with the subject and is in a convex lens shape or in a concave lens shape, according to the inner acoustic speed. The acoustic lens 26 makes the ultrasound entering the subject focus in the thickness direction (elevation direction) which is orthogonal to the cross-section of the picked-up image.

The acoustic lens 26 is formed of a soft polymer material having acoustic impedance about the same as that of the subject.

As for the material forming the acoustic lens 26, homopolymers such as silicone rubber, butadiene rubber, polyurethane rubber, epichlorohydrin rubber, etc., copolymer rubbers such as ethylene-propylene copolymer rubber made by copolymerizing ethylene and propylene, and the like, which are conventionally known, can be applied. Among these, it is preferred that silicone rubber or butadiene rubber is used.

As for the silicon rubber used in the embodiment, silicon rubber, fluorine silicon rubber, etc. are suggested. Especially, in light of the property of lens material, it is preferred to use silicone rubber. Silicon rubber generally refers to polyorganosiloxane having a molecular framework of Si—O bond and a plurality of organic groups are primary bonded to the Si atom. Usually, the main component is methylpolysiloxane and 90% or more of the entire organic groups are methyl groups. Silicon rubber in which a hydrogen atom, a phenyl group, a vinyl group and an allyl group are introduced in place of methyl groups may be used. Such silicon rubber can be obtained by mixing polyorganosiloxane having high polymerization degree and a hardener (vulcanising agent) such as benzoyl peroxide and curing the mixture by heating and vulcanization. Organic or inorganic filler substances such as silica powder, nylon powder and the like, vulcanization aid such as sulfur, zinc oxide and the like may be added as needed.

As for the butadiene rubber used in the embodiment, butadiene alone or polymer rubbers where butadiene and a small amount of styrene or acrylonitri are copolymerized, butadiene being the primary is suggested. Especially, in light of the property of lens material, it is preferred that butadiene rubber is used. Butadiene rubber refers to a synthetic rubber obtained by polymerization of butadiene having a conjugated double bond. Butadiene rubber may be obtained by single-butadiene having a conjugated double bond undergoing 1.4 to 1.2 polymerization. Butadiene rubber obtained by performing vulcanization by sulfur, etc. can be used.

The acoustic lens 26 according to the embodiment can be obtained by mixing a silicon rubber and a butadiene rubber and curing by vulcanization. For example, silicon rubber and butadiene rubber are mixed at an arbitrary ratio by mixing rollers, adding a vulcanization aid such as benzoyl peroxide and cross linking (curing) by heating and vulcanization. At this time, it is preferred that zinc oxide is added as the vulcanization aid. By using zinc oxide, vulcanization is facilitated and vulcanization time can be shortened without degrading the lens property. Other than zinc oxide, a colorant and other additives within the range that does not degrade the acoustic lens property may be added. With respect to the mixing ratio of silicon rubber and butadiene rubber, 1:1 is normally preferred in order to have acoustic impedance close to that of a human body, acoustic speed slower than a human body and small attenuation. However, the mixing rate may be changed arbitrarily.

As for silicon rubber, those sold on the market can be used. For example, KE 742U, KE752U, KE931U, KE941U, KE951U, KE961U, KE850U, KE555U, KE575U, etc. manufactured by Shin-Etsu Chemical Co. Ltd., TSE221-3U, TE221-4U, TSE2233U, XE20-523-4U, TSE27-4U, TSE260-3U and TSE-260-4U manufactured by Momentive Performance Materials Inc., SH35U, S55UA, SH831U, SE6749U, SE1120U and SE4704U manufactured by Dow Corning Toray Co., Ltd. and the like can be used.

In the embodiment, a rubber material such as the above mentioned silicon rubber can be used as the base (primary component) and inorganic fillers such as silica, alumina, titanium oxide, etc. and organic resins such as nylon can be blended according to the object such as acoustic speed adjustment, density adjustment or the like.

The layers constituting the ultrasound probe 2 are preferably layered via adhering layers (not shown in the drawing) therebetween. As for the adhesive for forming the adhering layers, an adhesive of epoxy group can be used.

Here, with respect to the ultrasound probe 2 of the embodiment, when $t_d$ refers to the layer thickness of the acoustic reflecting layer 23, $t_p$ refers to the layer thickness of the piezoelectric device 24, $t_{m(1)}, t_{m(2)} \ldots t_{m(n)}$ respectively refer to the thicknesses of the acoustic matching layers 25, the $1^{st}$ layer to the $n^{th}$ layer, counting from the piezoelectric device 24, $\lambda_{cd}$ refers to the wavelength of the ultrasound at the center frequency $f_c$ of the transmission and reception band of the ultrasound probe 2 that transmits inside the acoustic reflecting layer 23, $\lambda_{cp}$ refers to the wavelength of the ultrasound at the frequency $f_c$ that transmits inside the piezoelectric device 24 and $\lambda_{cm(1)}, \lambda_{cm(2)} \ldots \lambda_{cm(n)}$ respectively refer to the wavelengths of ultrasound at the frequency $f_c$ that transmits inside the acoustic matching layers 25, the $1^{st}$ layer to the $n^{th}$ layer, counting from the piezoelectric device 24, the following formula (1) is fulfilled.

$$\left( \frac{t_d}{\lambda_{cd}} + \frac{t_p}{\lambda_{cp}} + \frac{t_{m(1)}}{\lambda_{cm(1)}} + \frac{t_{m(2)}}{\lambda_{cm(2)}} + \ldots + \frac{t_{m(n)}}{\lambda_{cm(n)}} \right) \leq \frac{3}{4} \quad (1)$$

Below is the modification of the formula (1).

$$\left(\frac{t_d}{v_d}f_c + \frac{t_p}{v_p}f_c + \frac{t_{m(1)}}{v_{m(1)}}f_c + \frac{t_{m(2)}}{v_{m(2)}}f_c + \ldots + \frac{t_{m(n)}}{v_{m(n)}}f_c\right) \leq \frac{3}{4} \quad (2)$$

$$\left(\frac{t_d}{v_d} + \frac{t_p}{v_p} + \frac{t_{m(1)}}{v_{m(1)}} + \frac{t_{m(2)}}{v_{m(2)}} + \ldots + \frac{t_{m(n)}}{v_{m(n)}}\right)f_c \leq \frac{3}{4}$$

$$\left(\frac{t_d}{v_d} + \frac{t_p}{v_p} + \frac{t_{m(1)}}{v_{m(1)}} + \frac{t_{m(2)}}{v_{m(2)}} + \ldots + \frac{t_{m(n)}}{v_{m(n)}}\right) \leq \frac{3}{4} \times \frac{1}{f_c}$$

In each of the above expressions, $f_c$ refers to the center frequency of the transmission and reception band of the ultrasound probe. The transmission and reception band is a frequency response when ultrasound is transmitted toward a reflection board by the ultrasound probe and the returned reflected ultrasound is received by the ultrasound probe. Influence of the medium therebetween is not considered. When performing the actual measuring, by using degassed water, for example, as the medium between the probe and the reflection board, the measuring can be performed under very small influence of attenuation and the like. The center frequency of the transmission and reception band of the ultrasound probe is the center frequency of the band which is −6 dB from the maximum sensitivity of the transmission and reception band. Moreover, $v_d$ refers to the acoustic speed of ultrasound in the acoustic reflecting layer 23, $v_p$ refers to the acoustic speed of ultrasound in the piezoelectric device 24 and $v_{m(1)}$, $v_{m(2)}$ ... $v_{m(n)}$ respectively refers to the acoustic speeds of ultrasound in the acoustic matching layers 25, the $1^{st}$ layer to the $n^{th}$ layer, counting from the piezoelectric device 24.

Figure 4:
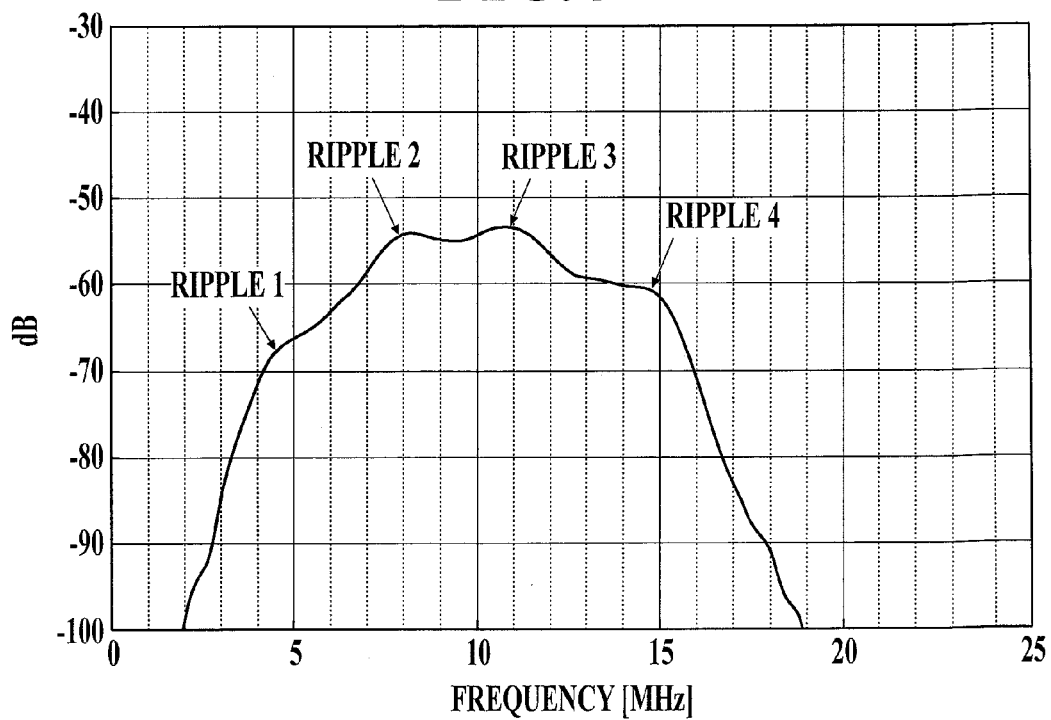
FIG. 4 is a diagram showing a frequency response of a conventional ultrasound probe constituted of a plurality of constituent layers.

An example of a frequency response of a conventional ultrasound probe formed of a plurality of constituent layers is shown in FIG. 4. In such frequency response, among the $1^{st}$ ripple counting from the low frequency side (ripple 1), the second ripple counting from the low frequency side (ripple 2), the $3^{rd}$ ripple counting from the low frequency side (ripple 3) and the $4^{th}$ ripple counting from the low frequency side (ripple 4), the resonance condition of the ripple 3 is expressed by the below formula.

$$\left(\frac{t_d}{\lambda_{xd}} + \frac{t_p}{\lambda_{xp}} + \frac{t_{m(1)}}{\lambda_{xm(1)}} + \frac{t_{m(2)}}{\lambda_{xm(2)}} + \ldots + \frac{t_{m(n)}}{\lambda_{xm(n)}}\right) = \frac{5}{4} \quad (3)$$

Below is the modification of the formula (3).

$$\left(\frac{t_d}{v_d}f_x + \frac{t_p}{v_p}f_x + \frac{t_{m(1)}}{v_{m(1)}}f_x + \frac{t_{m(2)}}{v_{m(2)}}f_x + \ldots + \frac{t_{m(n)}}{v_{m(n)}}f_x\right) = \frac{5}{4} \quad (4)$$

$$\left(\frac{t_d}{v_d} + \frac{t_p}{v_p} + \frac{t_{m(1)}}{v_{m(1)}} + \frac{t_{m(2)}}{v_{m(2)}} + \ldots + \frac{t_{m(n)}}{v_{m(n)}}\right)f_x = \frac{5}{4}$$

$$\left(\frac{t_d}{v_d} + \frac{t_p}{v_p} + \frac{t_{m(1)}}{v_{m(1)}} + \frac{t_{m(2)}}{v_{m(2)}} + \ldots + \frac{t_{m(n)}}{v_{m(n)}}\right) = \frac{5}{4} \times \frac{1}{f_x}$$

In the above individual formulas, $f_x$ refers to a resonance frequency. Further, $\lambda_{xd}$ refers to the wavelength of the ultrasound at the frequency $f_x$ which transmits inside the acoustic reflecting layer 23, $\lambda_{xp}$ refers to the wavelength of the ultrasound at the frequency $f_x$ which transmits inside the piezoelectric device 24 and $\lambda_{xm(2)}$, $\lambda_{xm(2)}$ ... $\lambda_{xm(n)}$ respectively refer to the wavelengths of ultrasound at the frequency $f_x$ which transmits inside the acoustic matching layers 25, the $1^{st}$ layer to the $n^{th}$ layer, counting from the piezoelectric device 24.

The following formulas can be obtained from the above formulas (2) and (4).

$$\frac{5}{4} \times \frac{1}{f_x} \leq \frac{3}{4} \times \frac{1}{f_c}$$

$$\frac{5}{3}f_c \leq f_x$$

Therefore, in a frequency response, the ripple 3 appears at a frequency higher than 5/3 times the center frequency $f_c$. In such way, by setting the layer thickness of each constituent layer of the ultrasound probe 2 so as to fulfill the formula (1), it is possible to make the $3^{rd}$ ripple counting from the low frequency side be outside the transmission and reception band in the frequency response, the transmission and reception band being defined as the range that is −6 dB from the maximum sensitivity.

Due to the layer thickness of each constituent layer of the ultrasound probe 2 being configured so as to fulfill the formula (1), the number of ripples which appear in the transmission and reception band can be reduced. As a result, the quality of the ultrasound image to be generated can be improved. Here, the lower limit of the total sum of t/λc values of the individual constituent layers is not specifically defined in the formula (1). It is sufficient that each of the acoustic reflecting layer, the piezoelectric device layer and the acoustic matching layer has a layer thickness sufficient to maintain its function.

For example, detail description will be given by taking the ultrasound probes 2A to 2G in which the layer thickness of each constituent layer is set as shown in table 1 as examples. With respect to the ultrasound probes 2A to 2G, the same material is used for the same constituent layers but they have different layer thicknesses. In table 1, the wavelength $\lambda_c$ in each composition layer when the center frequency is 10 MHz is also shown.

TABLE 1

| constituent layers of ultrasound probe | acoustic speed in constituent layers [m/s] | wavelength in constituent layers λc [μm] | ultrasound probe 2A layer thickness t [μm] | t/λ c | ultrasound probe 2B layer thickness t [μm] | t/λ c | ultrasound probe 2C layer thickness t [μm] | t/λ c | ultrasound probe 2D layer thickness t [μm] | t/λ c | ultrasound probe 2E layer thickness t [μm] | t/λ c | ultrasound probe 2F layer thickness t [μm] | t/λ c | ultrasound probe 2G layer thickness t [μm] | t/λ c |
|---|---|---|---|---|---|---|---|---|---|---|---|---|---|---|---|---|
| 3rd acoustic matching layer | 2270 | 227 | 55 | 0.24 | 50 | 0.22 | 45 | 0.20 | 40 | 0.18 | 33 | 0.15 | 35 | 0.15 | 25 | 0.11 |

TABLE 1-continued

| constituent layers of ultrasound probe | acoustic speed in constituent layers [m/s] | wavelength in constituent layers λc [μm] | ultrasound probe 2A layer thickness t [μm] | ultrasound probe 2A t/λc | ultrasound probe 2B layer thickness t [μm] | ultrasound probe 2B t/λc | ultrasound probe 2C layer thickness t [μm] | ultrasound probe 2C t/λc | ultrasound probe 2D layer thickness t [μm] | ultrasound probe 2D t/λc | ultrasound probe 2E layer thickness t [μm] | ultrasound probe 2E t/λc | ultrasound probe 2F layer thickness t [μm] | ultrasound probe 2F t/λc | ultrasound probe 2G layer thickness t [μm] | ultrasound probe 2G t/λc |
|---|---|---|---|---|---|---|---|---|---|---|---|---|---|---|---|---|
| 2nd acoustic matching layer | 2196 | 219.6 | 55 | 0.25 | 48 | 0.22 | 45 | 0.20 | 40 | 0.18 | 32 | 0.15 | 35 | 0.16 | 25 | 0.11 |
| 1st acoustic matching layer | 2699 | 269.9 | 65 | 0.24 | 59 | 0.22 | 55 | 0.20 | 48 | 0.18 | 54 | 0.20 | 40 | 0.15 | 30 | 0.11 |
| piezoelectric device | 4200 | 420 | 80 | 0.19 | 80 | 0.19 | 80 | 0.19 | 80 | 0.19 | 80 | 0.19 | 80 | 0.19 | 80 | 0.19 |
| acoustic reflecting layer | 6850 | 685 | 50 | 0.07 | 50 | 0.07 | 50 | 0.07 | 50 | 0.07 | 50 | 0.07 | 50 | 0.07 | 50 | 0.07 |
| total sum of t/λc values of constituent layers | — | | — | 1.00 | — | 0.92 | — | 0.87 | — | 0.80 | — | 0.75 | — | 0.73 | — | 0.60 |
| total sum of t/λc values of acoustic mathing layers | — | | — | 0.73 | — | 0.66 | — | 0.61 | — | 0.54 | — | 0.49 | — | 0.46 | — | 0.34 |

With respect to the frequency responses of the ultrasound probes 2A to 2G configured as described above, FIG. 5 shows a graph where the frequencies at which the ripples 1 to 4 appear are shown on the vertical axis and the total sums of t/$\lambda_c$ values of individual constituent layers of the ultrasound probes 2A to 2G (corresponding to the left side of the formula (1)) are shown on the horizontal axis. Further, FIG. 5 also shows the upper limits of the frequencies of the transmission and reception bands (a frequency at the maximum sensitivity −6 dB) in the frequency responses of the ultrasound probes 2A to 2G.

Figure 5:
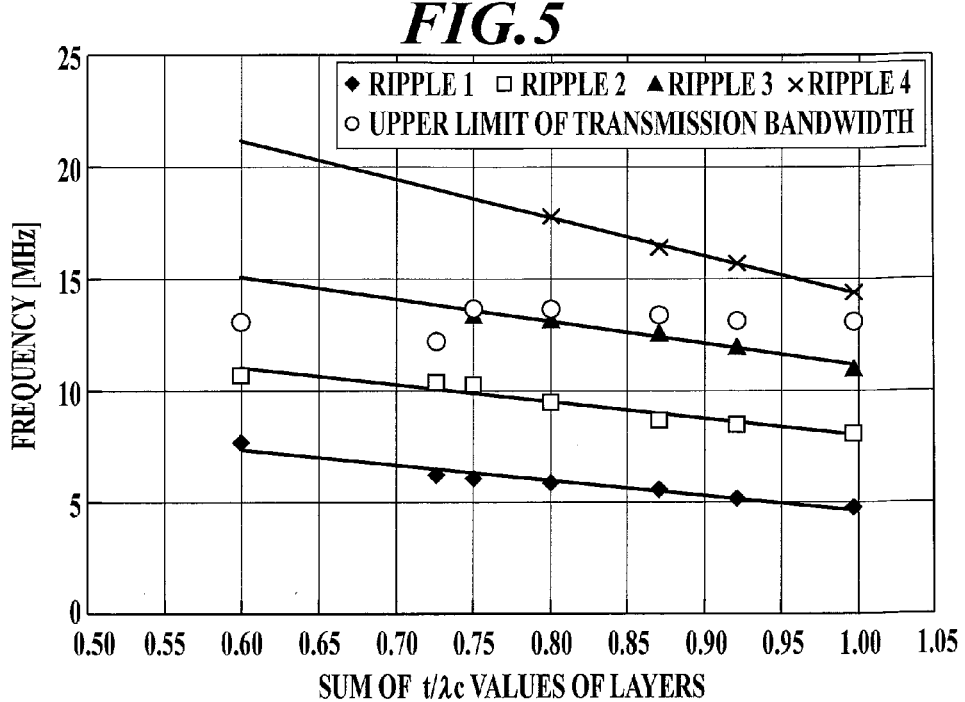
FIG. 5 shows plotting of frequencies where ripples appear in ultrasound probes having different configurations.

As shown in FIG. 5, when the total sum of t/$\lambda_c$ values of individual constituent layers is 0.75, the frequency at which the ripple 3 appears overlaps the upper limit of the transmission and reception band. Further, when the total sum of t/$\lambda_c$ values of individual constituent layers is smaller than 0.75, the frequencies at which the ripples 3 appear are greater than the upper limit of the transmission and reception band. Therefore, by making the total sum of t/$\lambda_c$ values of individual constituent layers be 0.75 or smaller, it is possible to make the ripple 3 exist outside the transmission and reception band.

Figure 6:
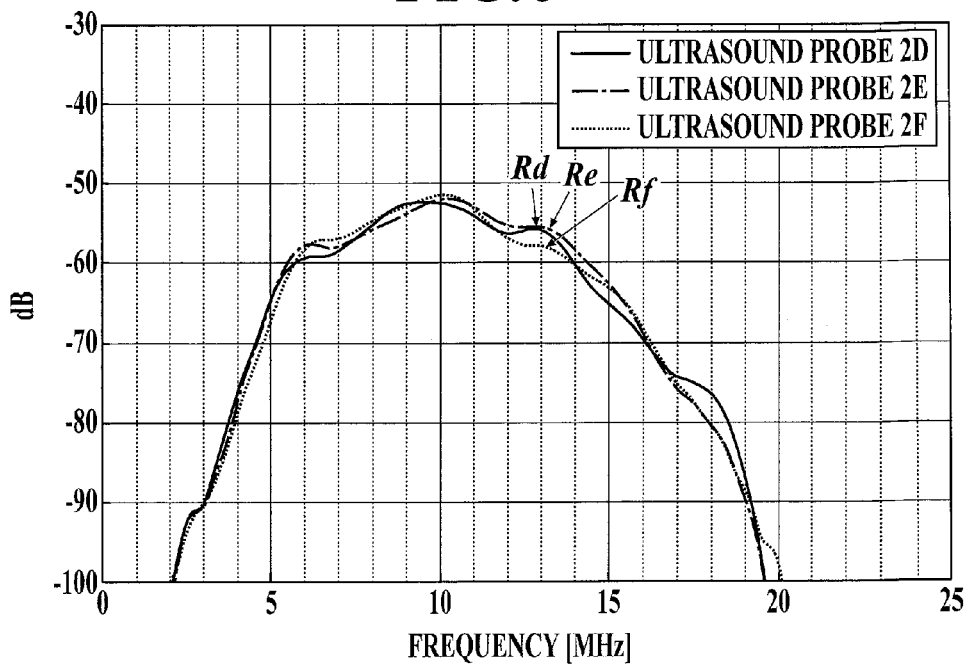
FIG. 6 shows frequency responses of ultrasound probes.

Further, FIG. 6 shows the frequency responses of the ultrasound probes 2D, 2E and 2F.

As described above, with respect to the ultrasound probe 2E wherein the total sum of t/$\lambda_c$ of the individual constituent layers is 0.75, the frequency at which the $3^{rd}$ ripple Re appears is about the same as the upper limit of the transmission and reception band (the frequency at the maximum sensitivity −6 dB). Further, with respect to the ultrasound probe 2F wherein the total sum of t/$\lambda_c$ of the individual constituent layers is 0.73, the frequency at which the $3^{rd}$ ripple Rf appears is greater than the upper limit of the transmission and reception band (the frequency at the maximum sensitivity −6 dB) and the ripple Rf is outside of the transmission and reception band. On the other hand, with respect to the ultrasound probe 2D wherein the total sum of t/$\lambda_c$ of the individual constituent layers is 0.08, the frequency at which the $3^{rd}$ ripple Rd appears is smaller than the upper limit of the transmission and reception band (the frequency at the maximum sensitivity −6 dB) and the ripple Rf is inside the transmission and reception band.

The ultrasound probe 2 of the embodiment is set so that the total sum of t/$\lambda_c$ values of individual acoustic matching layers 25 be 0.49 or smaller.

From the above, according to the embodiment, the layer thickness of the acoustic reflecting layer 23, the layer thickness of the piezoelectric device 24 and the layer thicknesses of the acoustic matching layers 25, the $1^{st}$ layer to the $n^{th}$ layer, counting from the back side, fulfill the formula (1). Therefore, the number of ripples included in the transmission and reception band of the ultrasound output from the ultrasound probe 2 can be reduces. Thereby, an ultrasound image of high quality can be obtained.

The entire disclosure of Japanese Patent Application No. 2013-140372 filed on Jul. 4, 2013 including description, claims, drawings, and abstract are incorporated herein by reference in its entirety.

What is claimed is:

1. An ultrasound probe, comprising:
   a piezoelectric device which transmits and receives ultrasound, the piezoelectric device having a predetermined layer thickness;
   n layers of acoustic matching layers having respective predetermined layer thicknesses and provided on a front side of the piezoelectric device, wherein the n layers comprise two layers or more;
   an acoustic lens which is provided on a front side of the acoustic matching layers; and
   an acoustic reflecting layer having a predetermined layer thickness and provided on a back side of the piezoelectric device,
   wherein the piezoelectric device, the acoustic matching layers, and the acoustic reflecting layer, fulfill the following formula (1):

$$\left( \frac{t_d}{\lambda_{cd}} + \frac{t_p}{\lambda_{cp}} + \frac{t_{m(1)}}{\lambda_{cm(1)}} + \ldots + \frac{t_{m(n)}}{\lambda_{cm(n)}} \right) \leq \frac{3}{4} \quad (1)$$

wherein $t_d$ represents the layer thickness of the acoustic reflecting layer, $t_p$ represents the layer thickness of the piezoelectric device, $t_{m(1)}, \ldots,$ and $t_{m(n)}$ respectively represent the layer thicknesses of the acoustic matching layers, such that $t_{m(1)}$ represents a $1^{st}$ layer among the acoustic matching layers, and $t_{m(n)}$ represents an $n^{th}$ layer among the acoustic matching layers, counting from the piezoelectric device, $\lambda_{cd}$ represents a wavelength of ultrasound that propagates inside the acoustic reflecting layer, the ultrasound being at a center frequency of a transmission and reception band of the ultrasound probe, $\lambda_{cp}$ represents a wavelength of the ultrasound that propagates inside the piezoelectric device, and $\lambda_{cm(1)}, \ldots,$ and $\lambda_{cm(n)}$ respectively represent wavelengths of the ultrasound that propagate inside the acoustic matching layers, such that $\lambda_{cm(1)}$ represents the wavelength of the ultrasound that propagates inside the $1^{st}$ layer among the acoustic matching layers, and $\lambda_{cm(n)}$ represents the wavelength of the ultrasound that propagates inside the $n^{th}$ layer among the acoustic matching layers, counting from the piezoelectric device.

2. The ultrasound probe of claim 1, wherein the ultrasound probe comprises three or more acoustic matching layers.

3. An ultrasound diagnostic imaging apparatus, comprising:
   the ultrasound probe of claim 1 which outputs transmission ultrasound toward a subject in accordance with a drive signal and which outputs a received signal by receiving reflection ultrasound from the subject; and
   an image generating unit which generates ultrasound image data for displaying an ultrasound image on a basis of the received signal output from the ultrasound probe.

4. A method for producing an ultrasound probe, comprising:
   providing a piezoelectric device which transmits and receives ultrasound, the piezoelectric device having a predetermined layer thickness;
   providing n layers of acoustic matching layers having respective predetermined layer thicknesses on a front side of the piezoelectric device, the n layers comprising two layers or more;
   providing an acoustic lens on a front side of the acoustic matching layers;
   providing an acoustic reflecting layer having a predetermined layer thickness on a back side of the piezoelectric device, and
   setting the layer thicknesses of the piezoelectric device, the acoustic matching layers, and the acoustic reflecting layer, so as to fulfill the following formula (1):

$$\left( \frac{t_d}{\lambda_{cd}} + \frac{t_p}{\lambda_{cp}} + \frac{t_{m(1)}}{\lambda_{cm(1)}} + \ldots + \frac{t_{m(n)}}{\lambda_{cm(n)}} \right) \leq \frac{3}{4} \quad (1)$$

wherein $t_d$ represents the layer thickness of the acoustic reflecting layer, $t_p$ represents the layer thickness of the piezoelectric device, $t_{m(1)}, \ldots,$ and $t_{m(n)}$ respectively represent the layer thicknesses of the acoustic matching layers, such that $t_{m(1)}$ represents a $1^{st}$ layer among the acoustic matching layers, and $t_{m(n)}$ represents an $n^{th}$ layer among the acoustic marching layers, counting from the piezoelectric device, $\lambda_{cd}$ represents a wavelength of ultrasound that propagates inside the acoustic reflecting layer, the ultrasound being at a center frequency of a transmission and reception band of the ultrasound probe, $\lambda_{cp}$ represents a wavelength of the ultrasound that propagates inside the piezoelectric device, and $\lambda_{cm(1)}, \ldots,$ and $\lambda_{cm(n)}$ respectively represent wavelengths of the ultrasound that propagates inside the acoustic matching layers, such that $\lambda_{cm(1)}$ represents the wavelength of the ultrasound that propagates inside the $1^{st}$ layer among the acoustic matching layers, and $\lambda_{cm(n)}$ represents the wavelength of the ultrasound that propagates inside the $n^{th}$ layer among the acoustic matching layers, counting from the piezoelectric device.

* * * * *